United States Patent

Fukuyama

[11] Patent Number: 6,024,100
[45] Date of Patent: Feb. 15, 2000

[54] HAIR RESTORING METHOD AND APPARATUS FOR CARRYING OUT THE SAME

[75] Inventor: Koki Fukuyama, Tokyo-To, Japan

[73] Assignee: Hochi Hiroshi, Tokyo-To, Japan

[21] Appl. No.: 09/022,298

[22] Filed: Feb. 11, 1998

[30] Foreign Application Priority Data

Jun. 30, 1997 [JP] Japan .................................... 9-173974

[51] Int. Cl.⁷ ................................................. A45D 19/00
[52] U.S. Cl. .................................. 132/200; 34/98; 34/99; 132/272
[58] Field of Search ..................................... 132/200, 202, 132/221, 270, 212, 272; 34/98, 99; 601/12, 17, 156, 166

[56] References Cited

U.S. PATENT DOCUMENTS

| | | | |
|---|---|---|---|
| 1,982,905 | 12/1934 | Davis | 132/202 |
| 2,655,145 | 10/1953 | Heger | 601/17 |
| 2,856,918 | 10/1958 | Kingery et al. | 601/166 |
| 3,177,868 | 4/1965 | Wallace et al. | 132/202 |
| 3,550,285 | 12/1970 | Omohundro | 132/212 |
| 3,575,181 | 4/1971 | Rudd | 132/272 |
| 5,228,431 | 7/1993 | Giarretto | 601/12 |

FOREIGN PATENT DOCUMENTS

8502997  7/1985  WIPO ..................................... 132/212

*Primary Examiner*—Todd E. Manahan
*Assistant Examiner*—Eduardo C. Robert
*Attorney, Agent, or Firm*—Ladas & Parry

[57] ABSTRACT

A hair restoring apparatus comprises a helmetlike cap having a sealing ring formed around a brim portion into which compressed air is supplied, and provided with an air inlet/outlet, steam inlets and hair restorer inlets. A pneumatic machine is connected to the air inlet/outlet of the cap and to the sealing ring formed around the brim portion of the cap by way of pipes, a steam generator is connected to the steam inlets of the cap by way of pipes, and a hair restorer supply unit for storing a hair restorer is connected to the hair restorer inlets of the cap by way of pipes. The cap is put on the head to form a sealed space between the cap and the head, steam is jetted into the sealed space after evacuating the latter to expand and to clean portions of the scalp around hair roots, a hair restorer is jetted into the evacuated, sealed space, and then compressed air is jetted into the sealed space to promote the penetration of the hair restorer into the portions of the scalp around hair roots.

9 Claims, 8 Drawing Sheets

HAIR RESTORING METHOD AND APPARATUS FOR CARRYING OUT THE SAME

BACKGROUND OF THE INVENTION

1. Field of the Invention

The present invention relates to a hair restoring method and an apparatus for carrying out the same.

2. Description of the Related Art

A conventional hair restoring method sprays the scalp with a hair restorer and massages the scalp with fingers to make the hair restorer penetrate portions of the scalp around hair roots. Another conventional hair restoring method sprays the scalp with a hair restorer and taps the head with a brush or the like to stimulate the scalp and to make the hair restorer penetrate portions of the scalp around hair roots.

When carrying out the foregoing conventional hair restoring methods, it is difficult to spray the scalp uniformly with the hair restorer and to make the hair restorer penetrate portions of the scalp around hair roots satisfactorily. Therefore the hair restorer is unable to fully exercise its effects even if the scalp is massaged with fingers or tapped with the brush or the like.

SUMMARY OF THE INVENTION

The present invention has been made in view of the foregoing problems in the conventional hair restoring methods and it is therefore an object of the present invention to provide an effective hair restoring method capable of solving the foregoing problems in the conventional hair restoring methods.

Another object of the present invention is to provide a hair restoring apparatus for carrying out the foregoing hair restoring method.

According to one aspect of the present invention, a hair restoring method comprises the steps of putting a cap on the head of a person after washing the latter, providing a sealed space between the cap and the head, exhausting air from the sealed space between the head and the cap using a pneumatic machine to evacuate the sealed space provide a vacuum, jetting steam into the evacuated, sealed space and jetting compressed air into the evacuated, sealed space using the pneumatic machine to expand portions of the scalp around hair roots and to remove body wastes, evacuating the sealed space again to provide a vacuum, jetting a hair restorer to make the hair restorer penetrate into expanded portions of the scalp around hair roots and, at the same time, jetting compressed air into the sealed space by the pneumatic machine to apply a pressure to the hair restorer staying in the portions of the scalp around hair roots so that the hair restorer is able to penetrate deep into the portions of the scalp around hair roots.

According to another aspect of the present invention, a hair restoring apparatus comprises: a helmetlike cap having a hollow sealing ring formed around a brim portion thereof into which compressed air is supplied. The cap is provided with an air inlet/outlet, a steam inlet and a hair restorer inlet; a pneumatic machine connected to the air inlet/outlet of the cap and to the sealing ring via pipes. A steam generator is also connected to the steam inlet of the cap by way of a pipe, and a hair restorer supply unit storing a hair restorer is connected to the hair restorer inlet of the cap by way of a pipe.

Thus the hair restorer, i.e., a mixture of a hair restoring agent and an emulsifier, such as a cream, can be made to penetrate efficiently into portions of the scalp around hair roots. Since the hair restoring apparatus comprises ordinary, simple devices including the pneumatic machine, the steam generator and the hair restorer supply unit, the hair restoring apparatus is simple in configuration, inexpensive and free from troubles.

The above and other objects, features and advantages of the present invention will become more apparent from the following description taken in connection with the accompanying drawings.

DESCRIPTION OF THE PREFERRED EMBODIMENT

Figure 1:
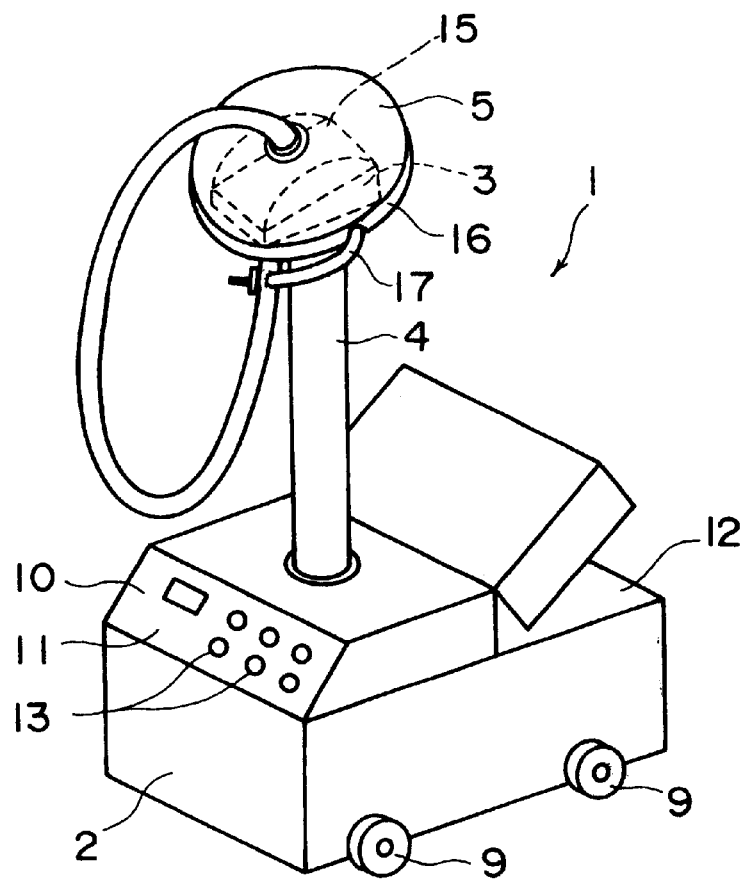
FIG. 1 is perspective view of a hair restoring apparatus for carrying out a hair restoring method in a preferred embodiment according to the present invention.

A hair restoring apparatus for carrying out a hair restoring method in a preferred embodiment according to the present invention will be described with reference to FIGS. 1 to 5E. As shown in FIG. 1, a hair restoring apparatus 1 comprises a cart 2, an auxiliary control panel 3 supported on the cart 2 by a hollow post 4, and a cap 5. As indicated in FIG. 4, functional components including a vacuum pump 6, i.e., a pneumatic machine, a steam generator 7 and a hair restorer supply unit 8 are carried on the cart 2. The cart 2 has a body having the shape of a rectangular parallelepiped, and wheels 9 are attached to the bottom of the body. A main control panel 11 is attached to an inclined wall 10 of the cart 2. An upper opening 12 (FIG. 1) is formed in half a section of the upper wall of the cart 2 to receive the cap 5 therethrough in the cart 2. The vacuum pump 6, the steam generator 7 and the hair restorer supply unit 8 are installed inside the cart 2. Rigid pipes, such as steel pipes, for connecting the vacuum pump 6, the steam generator 7 and the hair restorer supply unit 8 to the cap 5 are extended in the post 4.

Figure 2:
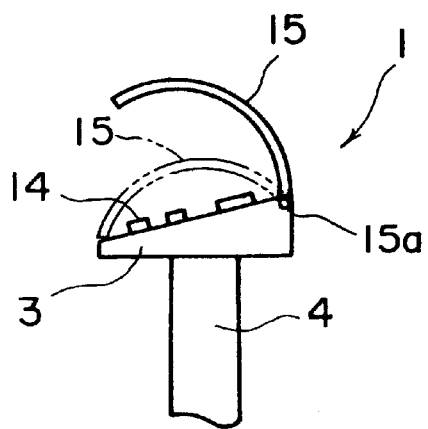
FIG. 2 is a side view of an auxiliary control panel.

On the main control panel 11 attached to the inclined wall 10 of the cart 2 are provided switches 13 for controlling the vacuum pump 6, the steam generator 7 and the hair restorer supply unit 8, and indicators for indicating the start and stop of the vacuum pump 6, the operating condition of the steam generator 7, the respective quantities of a hair restoring agent and an emulsifier for preparing a hair restorer, the operating condition of the hair restorer supply unit 8 and the like. As shown in FIG. 2, switches 14 which exercise the same functions as those of the switches 13 are arranged on the auxiliary control panel 3 and are interlocked with the switches 13. The switches 14 can be operated by an operator in a standing position. A curved cover 15 substantially resembling a dome is hinged to the upper wall of the cart 2 as shown in FIG. 2 so as to be turned about a hinge pin 15a to cover the auxiliary control panel 3. When the hair restoring apparatus 1 is not in use, the auxiliary control panel 3 is covered with the cover 15, and the cap 5 may be put on the cover 15 as shown in FIG. 1.

Figure 3:
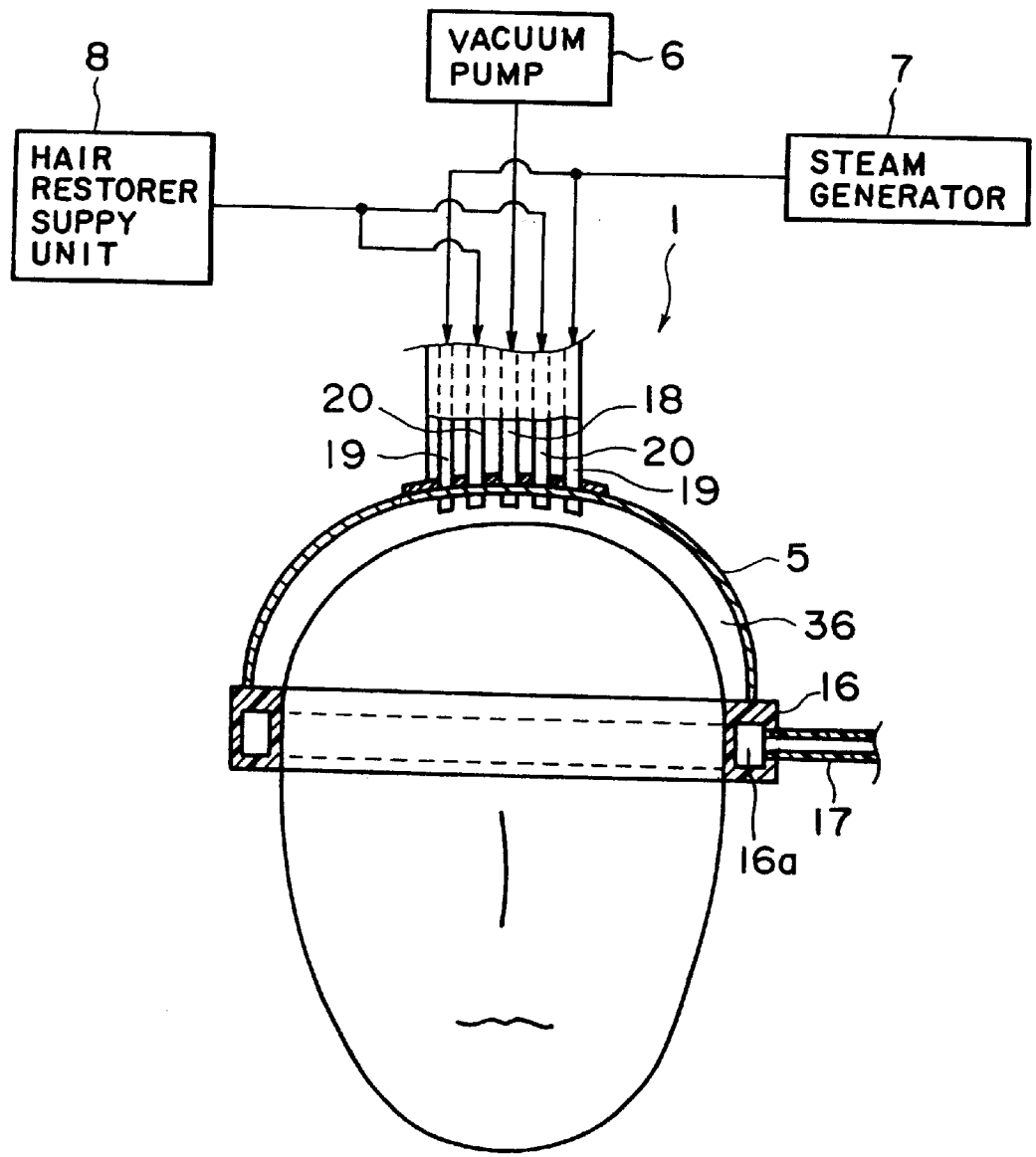
FIG. 3 is a longitudinal sectional view of a cap included in the hair restoring apparatus of FIG. 1.
Figure 4:
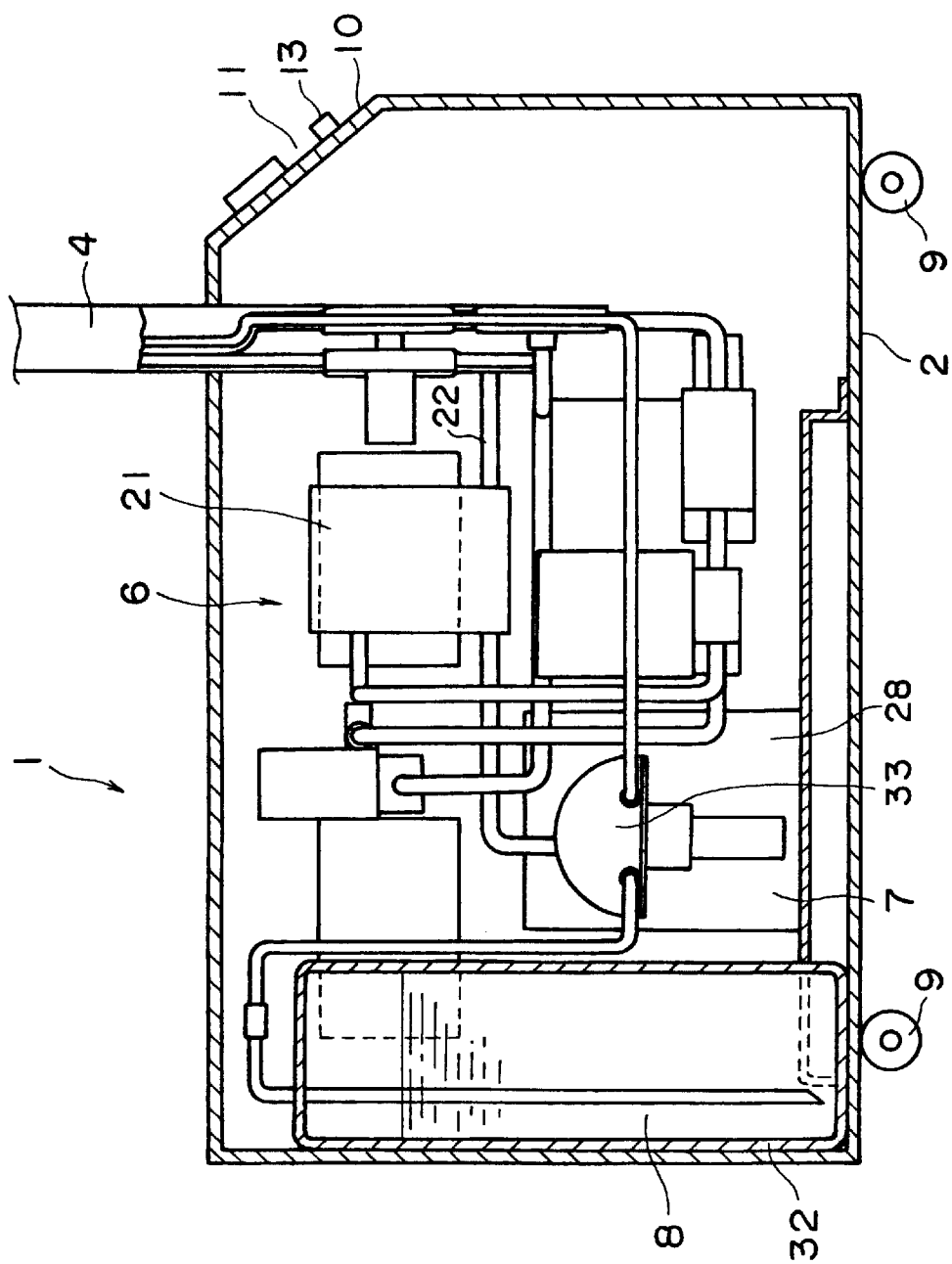
FIG. 4 is a longitudinal sectional view of functional unit included in the hair restoring apparatus of FIG. 1.

Referring to FIG. 3, the cap 5 has the shape of a helmet. A hollow, elastic sealing ring 16 having a cross section resembling a rectangular frame is attached to the brim of the cap 5, and one end of a flexible pipe 17 having the other end connected to the vacuum pump 6 is connected to an air inlet formed in an outer side wall of the sealing ring 16. One end of a flexible pipe 18 having the other end connected to the vacuum pump 6 is connected to an air inlet/outlet port formed in a top portion of the cap 5. Further, one end of each of flexible pipes 19 having the other ends connected to the steam generator 7 is connected to a steam inlet port formed in the top portion of the cap 5. Moreover, one end of each of flexible pipes 20 having the other ends connected to the hair restorer supply unit 8 is connected to a hair restorer inlet port formed in the top portion of the cap 5.

Figure 5A:
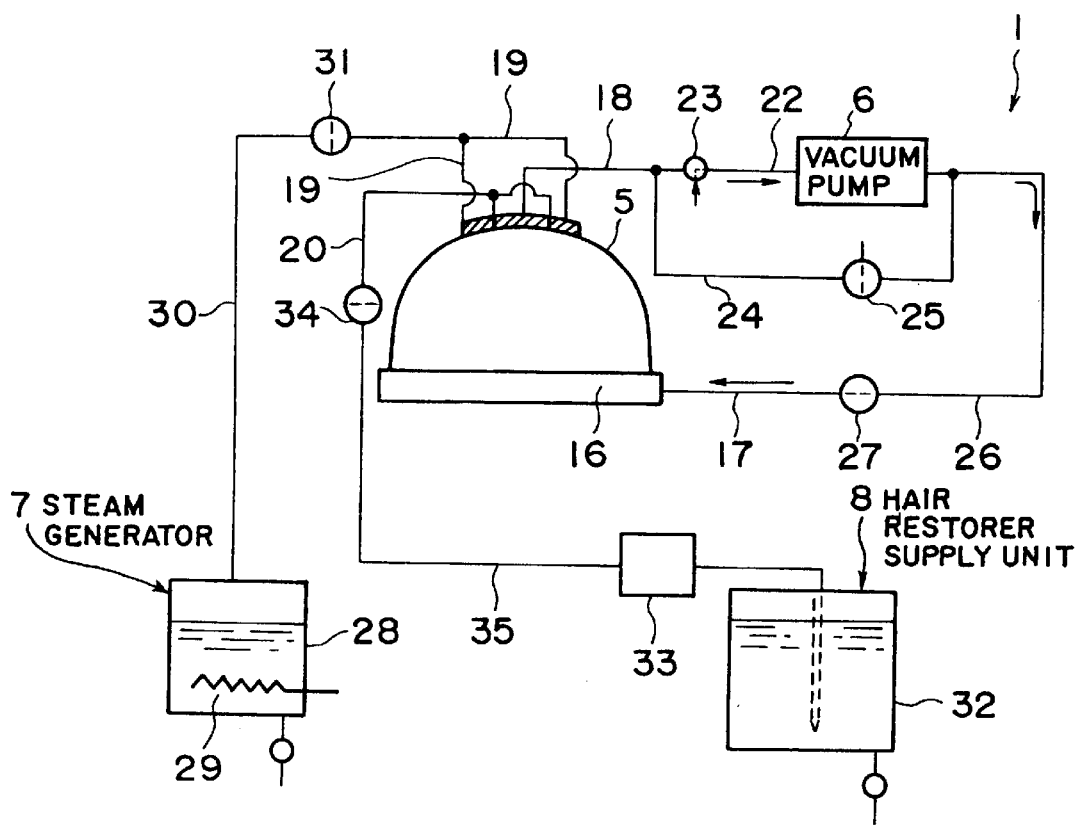
FIGS. 5A to 5E are diagrammatic views of a piping system included in the hair restoring apparatus of FIG. 1, showing sequential steps of operation of the apparatus.

The vacuum pump 6 is driven by a motor 21 mounted on the cart 2. The vacuum pump 6 is used for both sucking air and supplying compressed air. As shown in FIGS. 4 and 5A, vacuum pump 6 is connected via a rigid pipe 22, such as a steel pipe, extended in the post 4, and via the flexible pipe 18 connected to the rigid pipe 22 to the air inlet/outlet port formed in the top portion of the cap 5. A three-way valve 23 is placed in the rigid pipe 22. A rigid pipe 24, such as a steel pipe, has one end connected to one side of the vacuum pump 6 farther from the cap 5, and the other end connected to one side of the valve 23 nearer to the cap 5. A three-way valve 25 is placed in the rigid pipe 24. A valve 27 is placed in a rigid pipe 26, such as a steel pipe, having one end connected to one side of the vacuum pump farther from the cap 5 and the other end connected to the flexible pipe 17.

The steam generator 7 has a tank 28 mounted on the cart 2, and a heater 29 placed in the tank 28. The tank 28 is connected to the cap 5 by a rigid pipe 30, such as a steel pipe, and the flexible pipes 19. A valve 31 is placed in the rigid pipe 30.

The hair restorer supply unit 8 for supplying a hair restorer prepared by mixing a hair restoring agent, which may be a chemical agent available on the market, and an emulsifier has a tank 32 and a pump 33. The pump 33 is connected to the cap 5 by rigid pipe 35, such as a steel pipe, connected thereto and the flexible pipes 20 connected to the rigid pipe 35. A valve 34 is placed in the rigid pipe 34.

The pipes connected to the vacuum pump 6, the steam generator 7 and the hair restorer supply unit 8 and extended in the cart 2 and the post 4 are the rigid pipes, and those extended between the auxiliary control panel 3 and the cap 5 are flexible pipes.

The hair restoring method to be carried out by the hair restoring apparatus 1 will be described below. The head is first washed with a surface-active agent or the like, and the cap 5 is put on the head after thoroughly drying the head. Then, as shown in FIG. 5A, the three-way valve 23 is changed over to be communicated with the atmosphere, the valve 27 is opened and the vacuum pump 6 is started to supply compressed air into the hollow space 16a of the sealing ring 16 whereby the sealing ring 16 is inflated so as to be closely fitted on the head. Upon the increase of the pressure in the sealing ring 16 to a predetermined level, a pressure sensor provides a signal to stop the vacuum pump 6. Thus, a sealed space 36 (FIG. 3) is formed between the head and the cap 5.

Figure 5B:
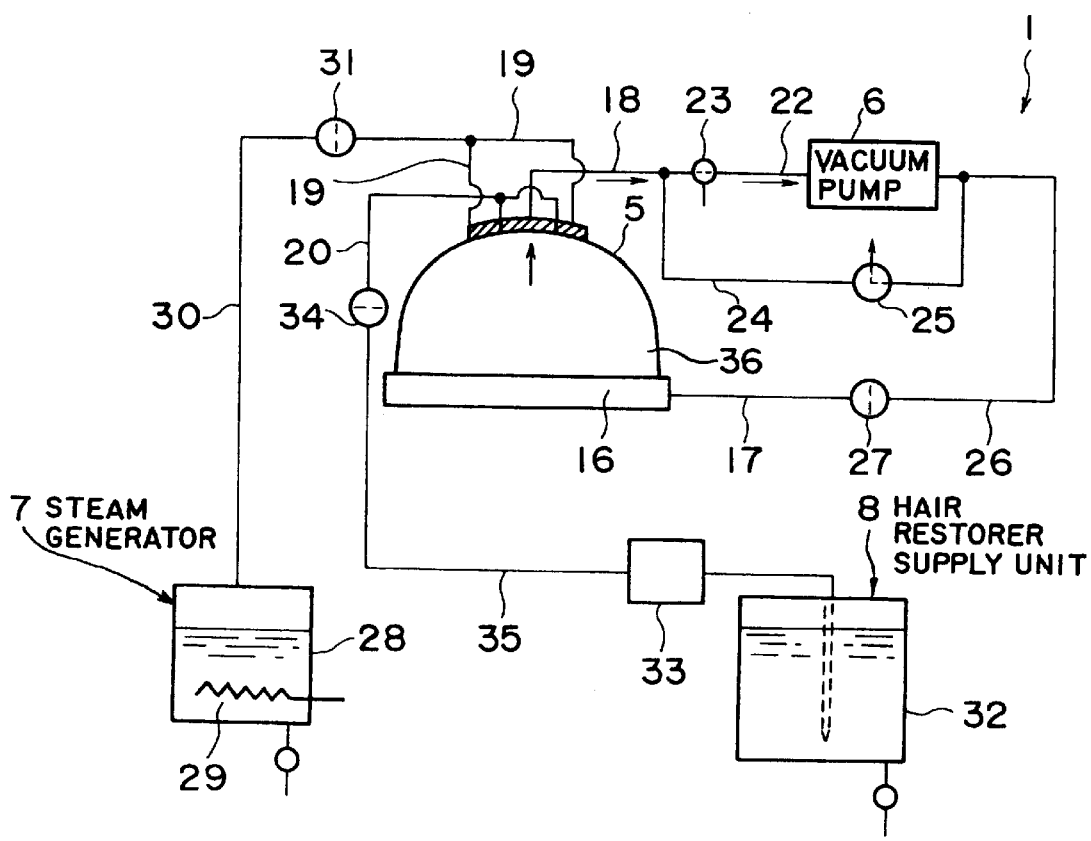
Figure 5C:
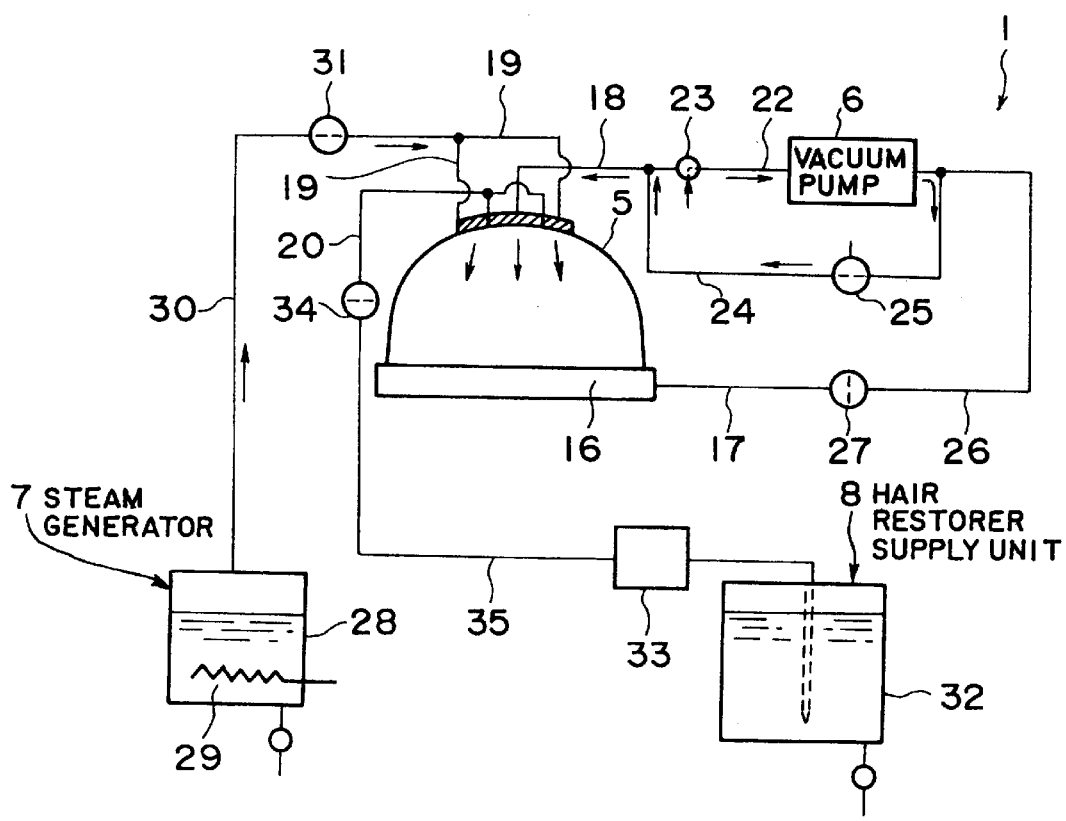
Figure 5D:
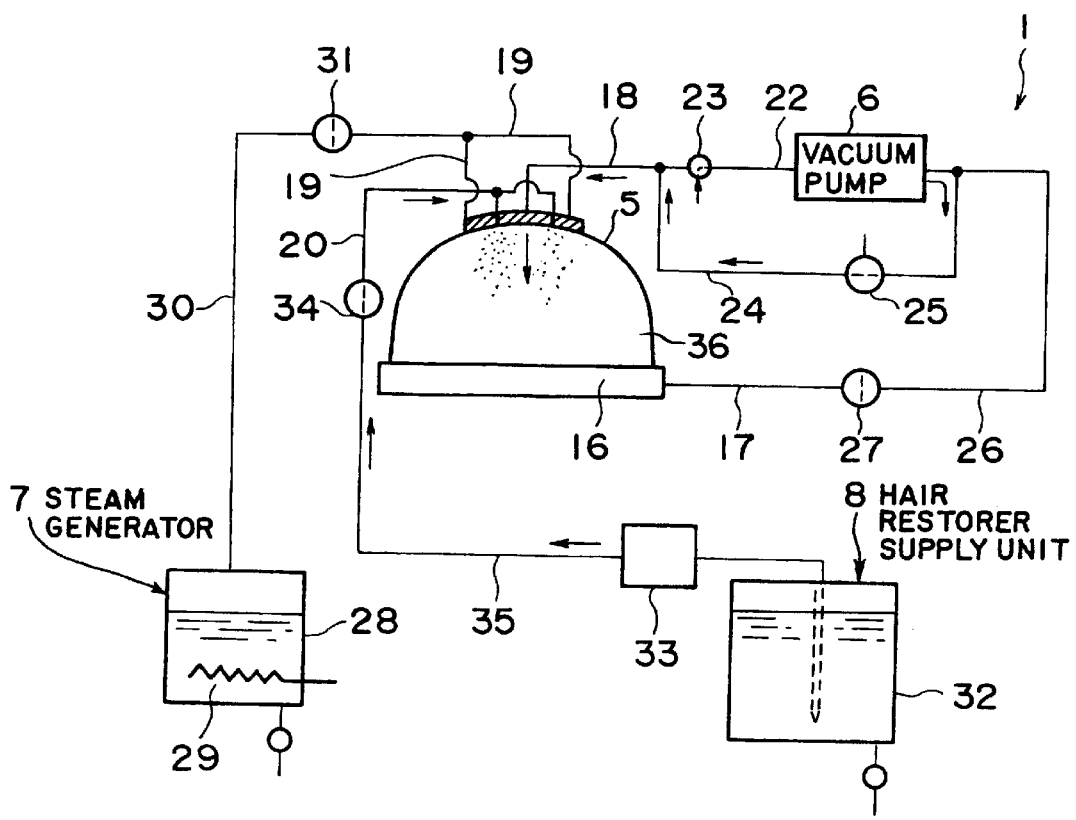

Subsequently, as shown in FIG. 5B, the valve 27 is closed, the valve 23 is changed over to communicate with the pipe 18 with the valve 25 changed over to communicate with the atmosphere, and the vacuum pump 6 is started to evacuate the sealed space 36. Then, as shown in FIG. 5C, the three-way valves 23 and 25 are changed over to the positions shown, the valve 31 is opened, and a scalp cleaning cycle including jetting steam of about 50° C. from the steam generator 7 into the space 36 and jetting compressed air from the vacuum pump 6 into the sealed space 36 is repeated a predetermined number of times at intervals of about five minutes to discharge waste skin and fat around hair roots, and the surface-active agent remaining on the scalp to the outside from the sealed space 36.

After repeating the scalp cleaning cycle the predetermined number of times, the vacuum pump 6 is stopped after the sealed space 36 has been evacuated to a predetermined vacuum in the state of FIG. 5B.

Then, a hair restoring cycle is started. In the hair restoring cycle shown in FIG. 5D, the valve 34 is opened and the pump 33 of the hair restorer supply unit 8 is driven to jet the hair restoring agent and the emulsifier in fine particles into the sealed space 36 so that the fine particles of the hair restoring agent and the emulsifier fill up the sealed space 36 and penetrate portions of the scalp around hair roots. In the meantime, the valve 34 is closed with the valve 25 opened and the vacuum pump 6 is driven to jet compressed air into the sealed space 36 to promote the penetration of the hair restoring agent and the emulsifier into the depths of the portions of the scalp around hair roots by a predetermined pressure. The hair restoring cycle is repeated a predetermined number of times in about twenty-five minutes.

Figure 5E:
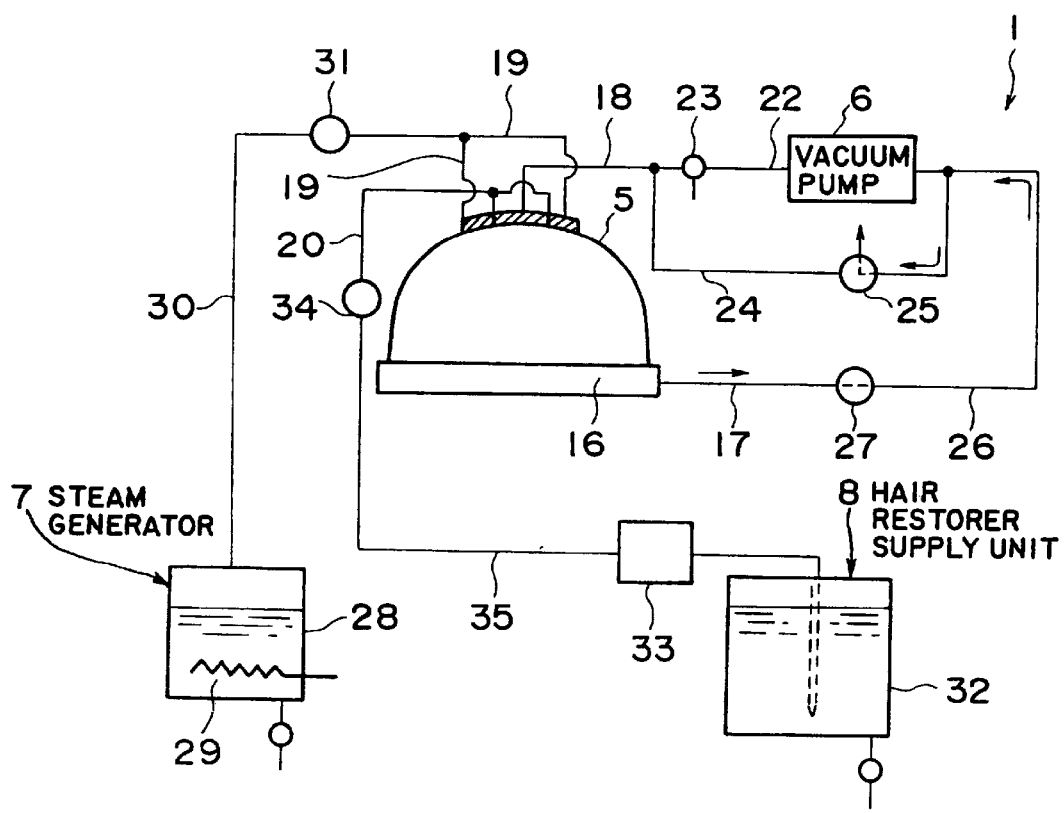

Then, as shown in FIG. 5E, the valve 25 is changed over to open the sealed space 36 to the atmosphere, and then the cap 5 is removed from the head. Thus, the steam applied to the scalp expands the portions of the scalp around hair roots to facilitate the penetration of the hair restoring agent and the emulsifier into the portion of the scalp around hair roots, and the compressed air promotes the penetration of the hair restoring agent and the emulsifier into the depths of the portions of the scalp around hair roots. The foregoing operations are carried out automatically under the control of a computer, and the operations of the valves are controlled automatically by signals provided by pressure switches. Any pneumatic machine may be used instead of the vacuum pump, provided that the pneumatic machine is capable of exhausting gases from the sealed space and of supplying compressed air into the sealed space.

Although the invention has been described in its preferred form with a certain degree of particularity, obviously many changes and variations are possible therein. It is therefore to be understood that the present invention may be practiced otherwise than as specifically described herein without departing from the scope and spirit thereof.

What is claimed is:

1. A hair restoring method comprising the steps of:

putting a cap on the head of a person after washing the latter;

providing a sealed space between the cap and the head;

exhausting air from the sealed space between the head and the cap by a pneumatic machine to evacuate the sealed space in a vacuum;

jetting steam into the evacuated, sealed space and jetting a compressed air into the evacuated, sealed space by the pneumatic machine to expand portions of the scalp around hair roots and to remove body wastes;

evacuating the sealed space again in a vacuum;

jetting a hair restorer to make the hair restorer penetrate into expanded portions of the scalp around hair roots and, at the same time, jetting compressed air into the sealed space by the pneumatic machine to apply a pressure to the hair restorer staying in the portions of the scalp around hair roots so that the hair restorer is able to penetrate deep into the portions of the scalp around hair roots.

2. The hair restoring method according to claim 1, wherein said step of providing a sealed space comprises supplying compressed air into a sealing ring formed around the brim portion of the cap into close contact with the circumference of the head in order that the sealed space is formed between the head and the cap.

3. A hair restoring apparatus comprising:

a helmetlike cap having a top portion, a brim portion and a sealing ring formed around the brim portion, with a hollow space into which compressed air is supplied, said cap being provided in said top portion with an air inlet/outlet, a steam inlet and a hair restorer inlet;

a pneumatic machine connected to the air inlet/outlet of the cap and to the sealing ring via pipes;

a steam generator connected to the steam inlet of the cap by way of a pipe; and a hair restorer supply unit storing a hair restorer and connected to the hair restorer inlet of the cap by way of a pipe.

4. The hair restoring apparatus according to claim 3, further comprising:

a cart having said pneumatic machine, steam generator and hair restorer supply unit mounted thereon; and said pipes connected to said air inlet/outlet, said steam inlet and said hair restorer inlet of the cap including flexible pipes.

5. The hair restoring apparatus according to claim 4, further comprising:

a control panel on the cart.

6. The hair restoring apparatus according to claim 4, further comprising:

a hollow post erected on the cart and having therein parts of said pipes connected to said air inlet/outlet, said steam inlet and said hair restorer inlet of the cap.

7. The hair restoring apparatus according to claim 6, wherein said flexible pipes extend from a top of said hollow post.

8. The hair restoring apparatus according to claim 5, further comprising:

an auxiliary control panel provided on a top of said hollow post.

9. The hair restoring apparatus according to claim 8, further comprising:

an openable cover provided on said auxiliary control panel, on which cover said cap is mountable when not in use, said cover being shaped to receive the cap thereon.

\* \* \* \* \*

UNITED STATES PATENT AND TRADEMARK OFFICE
CERTIFICATE OF CORRECTION

PATENT NO.     : 6,024,100
DATED          : February 15, 2000
INVENTOR(S)    : Koki Fukuyama It is certified that error appears in the above-identified patent and that said Letters Patent is hereby corrected as shown below:

<u>Title page,</u>
Item [73], Assignee, "Hochi Hiroshi" should read -- Hiroshi Hochi --.

Signed and Sealed this

Twenty-seventh Day of April, 2004

JON W. DUDAS
*Acting Director of the United States Patent and Trademark Office*